United States Patent
Khalil et al.

(10) Patent No.: US 9,033,913 B2
(45) Date of Patent: May 19, 2015

(54) BREASTSHIELD UNIT

(75) Inventors: Gamal Khalil, Baar (CH); René Fischer, Zurich (CH); André Schlienger, Maschwanden (CH)

(73) Assignee: MEDELA HOLDING AG, Baar (CH)

( * ) Notice: Subject to any disclaimer, the term of this patent is extended or adjusted under 35 U.S.C. 154(b) by 384 days.

(21) Appl. No.: 13/535,671

(22) Filed: Jun. 28, 2012

(65) Prior Publication Data

US 2013/0023821 A1  Jan. 24, 2013

(30) Foreign Application Priority Data

Jul. 18, 2011 (CH) ........................................ 1201/11

(51) Int. Cl.
*A61M 1/06* (2006.01)
*A61M 1/00* (2006.01)

(52) U.S. Cl.
CPC ............... *A61M 1/06* (2013.01); *A61M 1/0072* (2014.02); *A61M 1/064* (2014.02); *A61M 1/0049* (2013.01)

(58) Field of Classification Search
CPC ..... A61M 1/06; A61M 1/066; A61M 1/0072; A61M 1/064; A61M 1/0037; A61M 1/062; A61M 1/0031; A61M 1/0049; A61M 2210/1007; A61J 9/001; A61J 13/00; A61J 9/00; A61J 9/005; A61J 9/085; A41C 3/04
USPC .................................................. 604/74, 119
See application file for complete search history.

(56) References Cited

U.S. PATENT DOCUMENTS

| | | | |
|---|---|---|---|
| 4,270,538 A | 6/1981 | Murphy | |
| 6,379,327 B2 | 4/2002 | Lundy | |
| 6,440,100 B1 | 8/2002 | Prentiss | |
| 6,461,324 B1 * | 10/2002 | Schlensog | 604/74 |
| 7,223,255 B2 | 5/2007 | Myers et al. | |
| 8,109,901 B2 * | 2/2012 | Bryan et al. | 604/74 |
| 2001/0038799 A1 * | 11/2001 | Silver et al. | 417/515 |
| 2008/0039781 A1 | 2/2008 | Bjorge | |
| 2008/0262420 A1 | 10/2008 | Dao et al. | |

(Continued)

FOREIGN PATENT DOCUMENTS

| | | |
|---|---|---|
| EP | 2138197 | 12/2009 |
| WO | 2008/057218 | 5/2008 |

(Continued)

OTHER PUBLICATIONS

Swiss Search Report for Swiss Patent App. No. 1201/11, dated Nov. 11, 2011.

(Continued)

*Primary Examiner* — Nicholas Lucchesi
*Assistant Examiner* — Diva K Chander
(74) *Attorney, Agent, or Firm* — McDonnell Boehnen Hulbert & Berghoff LLP (57) ABSTRACT

A breastshield unit for expressing human breastmilk has a receiving part for receiving a human nipple, an underpressure chamber for applying an under-pressure to the nipple, wherein the receiving part opens into this underpressure chamber, and a membrane for generating an underpressure in the underpressure chamber. The membrane is designed in one or more pieces and at least partially surrounds the receiving part. This breastshield unit permits a separation of media in the area near the breast. It is small and easy to clean and is suitable in particular for use as a hands-free breastshield unit.

33 Claims, 8 Drawing Sheets

(56) References Cited

U.S. PATENT DOCUMENTS

2010/0121266 A1*  5/2010  Bryan et al. ............... 604/74
2011/0071466 A1*  3/2011  Silver et al. ............... 604/74

FOREIGN PATENT DOCUMENTS

WO  2008/137678  11/2008
WO  2011/035448  3/2011
WO  2011/037841  3/2011

OTHER PUBLICATIONS

International Search Report for int. App. No. PCT/CH2012/000164, completed Sep. 24, 2012.

* cited by examiner

BREASTSHIELD UNIT

CROSS REFERENCE TO RELATED APPLICATIONS

The present application claims priority to Swiss Patent Application No. 1201/11, filed Jul. 18, 2011, the entire disclosure contents of which is herewith incorporated by reference into the present application.

TECHNICAL FIELD

The present invention relates to a breastshield unit.

BACKGROUND

Devices for expressing human breastmilk are well known. Manually or electrically operated vacuum pumps are connected directly or via vacuum lines to a breastshield, which is used to receive a part of the mother's breast including the nipple.

WO 2008/057218 discloses a breastpump with a vacuum pump, a vacuum line, a base, and a funnel-shaped and stiff breastshield that can be secured on this base. The vacuum line connects the vacuum pump to the base. In order to protect the vacuum line and the vacuum pump from contamination, a barrier in the form of a large-surface membrane is arranged in the base. This membrane is arranged in a pump chamber, in which the under-pressure generated by the pump unit is transferred to the other side of the membrane.

WO 2011/037841 likewise describes a breastpump with a base part, to which it is possible to connect a funnel-shaped and stiff breastshield, a vacuum line for connection to the vacuum pump, and a milk collection container. The base part likewise has a membrane in order to protect the vacuum line.

U.S. Pat. No. 7,223,255 and WO 2008/137678 disclose so-called hands-free breast pumps, which can be worn under the bra. The breast interface, which is placed sealingly on the mother's breast, serves at the same time as a membrane of the vacuum pump. That is to say, the pump chamber of the vacuum pump is formed between the soft breast interface and the mother's breast.

U.S. Pat. No. 6,379,327 discloses another hands-free breastpump. Here, a small breastshield is arranged in the bra. From this breastshield, a vacuum line leads to a vacuum pump unit and a milk line leads to a milk collection container. Vacuum pump unit and milk collection container are arranged in a strap, which the mother wears around her waist.

In US 2008/0262420, a flexible bag for collecting the milk is secured on a stiff breastshield, and both are worn in the bra. A vacuum line opening out in the upper area of the breastshield leads to a vacuum pump worn in a strap.

U.S. Pat. No. 6,440,100 also discloses a hands-free breastpump. Here too, a vacuum line leads from a breastshield to a vacuum pump. This line is at the same time used as a milk line.

US 2008/0039781 relates to a support device for stiff breastshields, wherein the support device can be secured on the bra.

U.S. Pat. No. 4,270,538 discloses a breastshield designed to catch a spontaneous flow of breastmilk. The breastshield has a soft breast interface and, connected to the latter, a cap into which the milk can flow.

WO 2011/035448 discloses a breastpump for expressing human breastmilk, in which a vacuum line is used at the same time as a milk line and in which a membrane of a diaphragm vacuum pump serves as media separator.

DISCLOSURE OF THE INVENTION

It is an object of the invention to create an improved device for expressing human breastmilk.

The breastshield unit according to the invention for expressing human breastmilk has a receiving part for receiving a human nipple, an underpressure chamber for applying an underpressure to the nipple, wherein the receiving part opens into this underpressure chamber, and a membrane for generating an underpressure in the underpressure chamber.

According to the invention, the membrane is designed in one or more pieces, and it at least partially surrounds the receiving part.

Alternatively or in addition, the membrane, viewed in the direction of extension of a centre axis of the receiving part, is arranged on a side of the under-pressure chamber facing towards the nipple. This indication of position does not mean that the membrane separates the underpressure chamber from the nipple but that the membrane is not, as is known in the prior art, arranged farther from the nipple than the underpressure chamber in the direction of the centre axis. This arrangement of underpressure chamber and membrane permits the formation of a compact breastshield unit.

Also alternatively or in addition, the breastshield unit according to the invention has a milk port for connecting the underpressure chamber to a milk collection container. The membrane for generating an underpressure in the underpressure chamber is, viewed in the direction of extension of a centre axis of the receiving part, arranged on a side of this milk port facing towards the mother's breast. Here too, this indication of position once again signifies what has been said in the paragraph above. The same advantage as in the previous example is likewise achieved here.

The breastshield unit according to the invention can be made extremely small and compact by virtue of the special arrangement of the membrane. A large-surface membrane can nevertheless be used, such that a small stroke of the membrane is sufficient to ensure that an underpressure necessary for the expression of milk is generated in the area of the breastshield. The stroke requirement is also reduced because the dead volume is minimized, i.e. the underpressure chamber in the area of the nipple has a small volume.

The large diameter of the membrane also facilitates the assembly and also the cleaning of the device. The separation of media, i.e. the separation of air or vacuum and milk, is also optimally ensured by virtue of the large surface of the membrane.

The membrane can be designed in one or more pieces. It preferably contains an opening in the shape of a circle or partial circle. This opening is preferably arranged in the centre. In a preferred embodiment, the receiving part passes through the opening.

In a preferred embodiment, the membrane is formed in one piece and has an annular shape. This membrane has the advantage that it is easy to produce, easy to assemble and easy to clean. It also has a large surface.

In another preferred embodiment, the membrane is composed of at least two individual parts, preferably three individual parts. These individual parts, in the assembled state, enclose a circle or a partial circle. This embodiment has the advantage that the rest of the design of the breastshield unit does not have to be adapted to an annular shape of the membrane, and instead the membrane parts can be adapted to the shape of the unit. The pump chamber can be divided according to the division of the membrane, or can be designed as a continuous pump chamber. The individual membrane parts can be of identical design, or can have different shapes and sizes.

In another preferred embodiment, only a single membrane part is present which, on one side, has an indentation in the shape of a partial circle. In the assembled state, this indentation is assigned to the receiving part and preferably has the receiving part passing through it. The edge of the membrane opposite this indentation is preferably likewise curved. The membrane can, for example, have a kidney shape.

In its rest position, i.e. with no underpressure applied, the one-piece annular membrane preferably has a frustoconical shape, such that it is optimally adapted to the shape of the mother's breast. The parts of the multi-piece membrane and the one-piece membrane shaped as a partial circle are preferably designed as parts of such a frustum. The membrane is made of a soft flexible material, in particular of silicone. A hardness of 60 Shore A is preferred.

The membrane is preferably held movably in a membrane housing. For this purpose, for example, the membrane can have, on its edge, a circumferential bead that is held in a corresponding seat of the membrane housing.

The membrane housing is preferably in several parts, in particular in two parts, with a breast-side part and a part facing away from the breast.

In a preferred embodiment, the breastshield unit according to the invention has a breast interface for placing on a mother's breast, the breast interface can be secured on a housing shell enclosing the membrane. The housing shell can be formed by a membrane housing part facing away from the breast, or by a part likewise enclosing this membrane housing part. The breast interface preferably replaces the normally used breastshield.

In a preferred embodiment, the breast interface is made of a soft material, in particular of silicone, and preferably has a Shore A hardness of 50.

In a preferred embodiment, the breast interface has a frustoconical or cylindrical first stub for receiving the nipple, wherein this first stub can be connected to a second stub of the underpressure chamber, and wherein this first stub and the second stub form the receiving part. The frustoconical part is preferably very short and designed with a large opening angle and a large surface, such that the breastshield usually touches only the areola and, possibly, also adjoining tissue.

The breast interface can be a part separate from the membrane, or can be connected in one piece to this membrane.

The membrane housing is preferably held movably relative to the housing shell. The membrane housing preferably forms a membrane suspension with a membrane arranged therein, which are arranged movably inside this housing shell. This has the advantage that, when the breast interface deforms during use, the membrane housing is not also deformed, and therefore the pump chamber and the underpressure chamber, i.e. the dead volume, remain unchanged in terms of their volume. This ensures a uniform pump output during use.

The breastshield unit according to the invention can be designed as a hands-free unit and worn under a bra. In a preferred embodiment, a milk collection container is integrated in the housing of the unit or can be coupled directly thereto. Alternatively or in addition, a manually controlled or a motor-driven vacuum pump can be integrated in the housing or connected directly thereto. When a motor-driven vacuum pump is used, a power supply is preferably also integrated in the housing or connected directly thereto.

In another preferred embodiment, the breastshield unit is connected via external lines to a milk collection container and/or to an external vacuum source.

Further embodiments are set forth in the dependent claims.

BRIEF DESCRIPTION OF THE FIGURES

Preferred embodiments of the invention are described below with reference to the drawings, which are provided only for explanatory purposes and are not to be interpreted as limiting the invention. Identical parts are designated by identical reference signs. In the drawings.

DETAILED DESCRIPTION

FIGS. 1 to 5 show a first embodiment of a breastshield unit 9 according to the invention.

The breastshield unit 9 has a breast interface 1 for placing on a human mother's breast and a shell 6 on which the breast interface 1 is secured releasably. The breast interface 1 is preferably round, with a circumferential securing lip 11 surrounding a circumferential securing flange 62 of the shell 6.

The breast interface 1 is made of a soft elastic material, in particular of silicone, and conforms to the shape of the mother's breast. The breast interface 1 has an opening 13, which is surrounded by a frustoconical or cylindrical stub 10. This opening 13 is preferably arranged centrally within the breast interface 1.

The shell 6 is preferably dome-shaped or hemispherical. The shell 6 is preferably in one piece and rigid, and usually made of a plastic.

In the illustrative embodiment according to FIGS. 1 to 5, the shell 6 has a first through-opening 60, through which a vacuum line 80, here a silicone hose, is connected to a corresponding port of the breastshield unit. The connection is preferably releasable. This vacuum line 80 leads to an external suction pump unit 8, in which a vacuum pump is arranged. This is preferably a motor-driven vacuum pump. The vacuum pump can be mains-operated. In addition or alternatively, a power source can be integrated in the suction pump unit. The suction pump unit 8 usually has control elements and a display 84.

The shell 6 is provided with a second through-opening 61. A first end of a milk line 70, here likewise a silicone hose, can be connected releasably to a milk port of the breastpump unit 9 via this through-opening 61. The other end of the milk line 70 is connected releasably to an external milk collection container 7.

Figure 1:
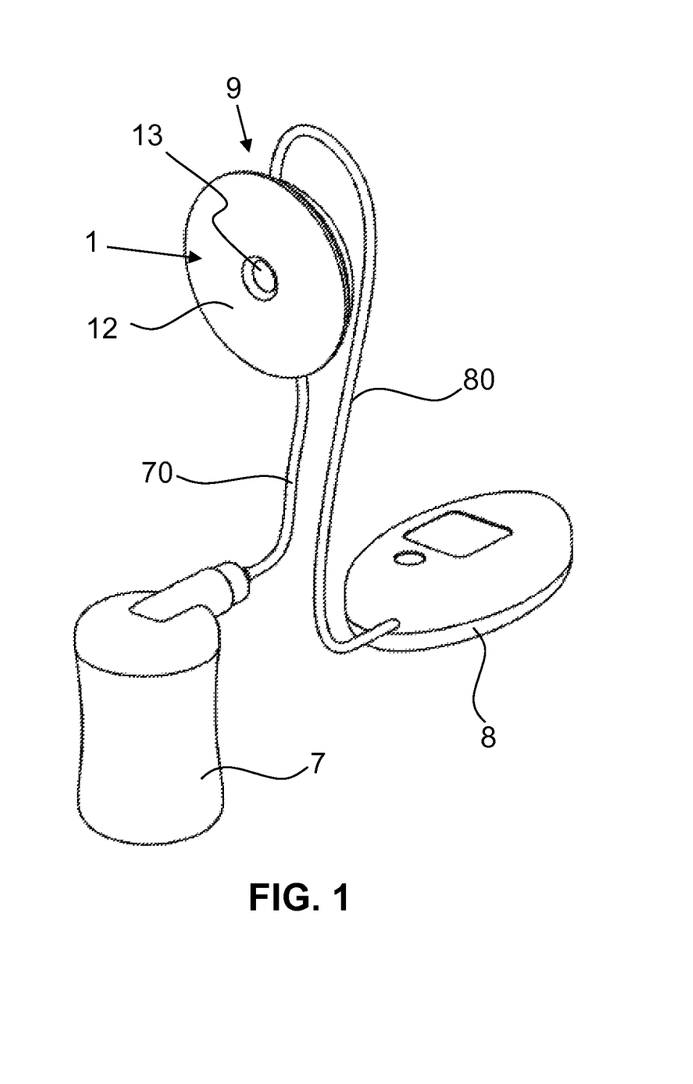
FIG. 1 shows a schematic view of a breastpump with a breastshield unit according to the invention.
Figure 2:
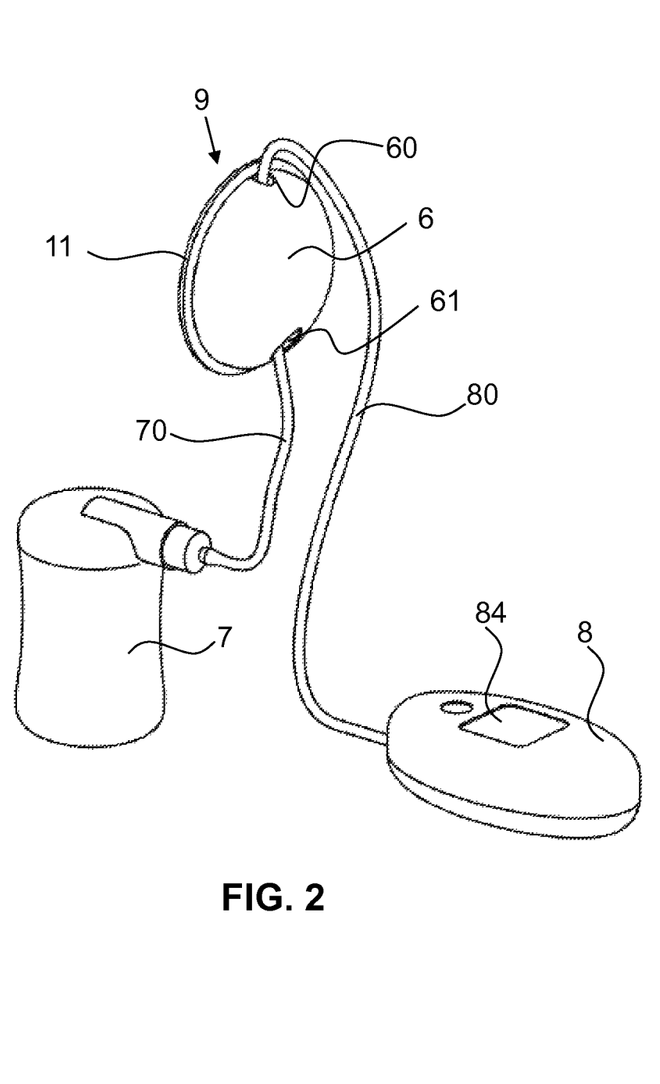
FIG. 2 shows the breastpump according to FIG. 1 in a second perspective view.
Figure 3:
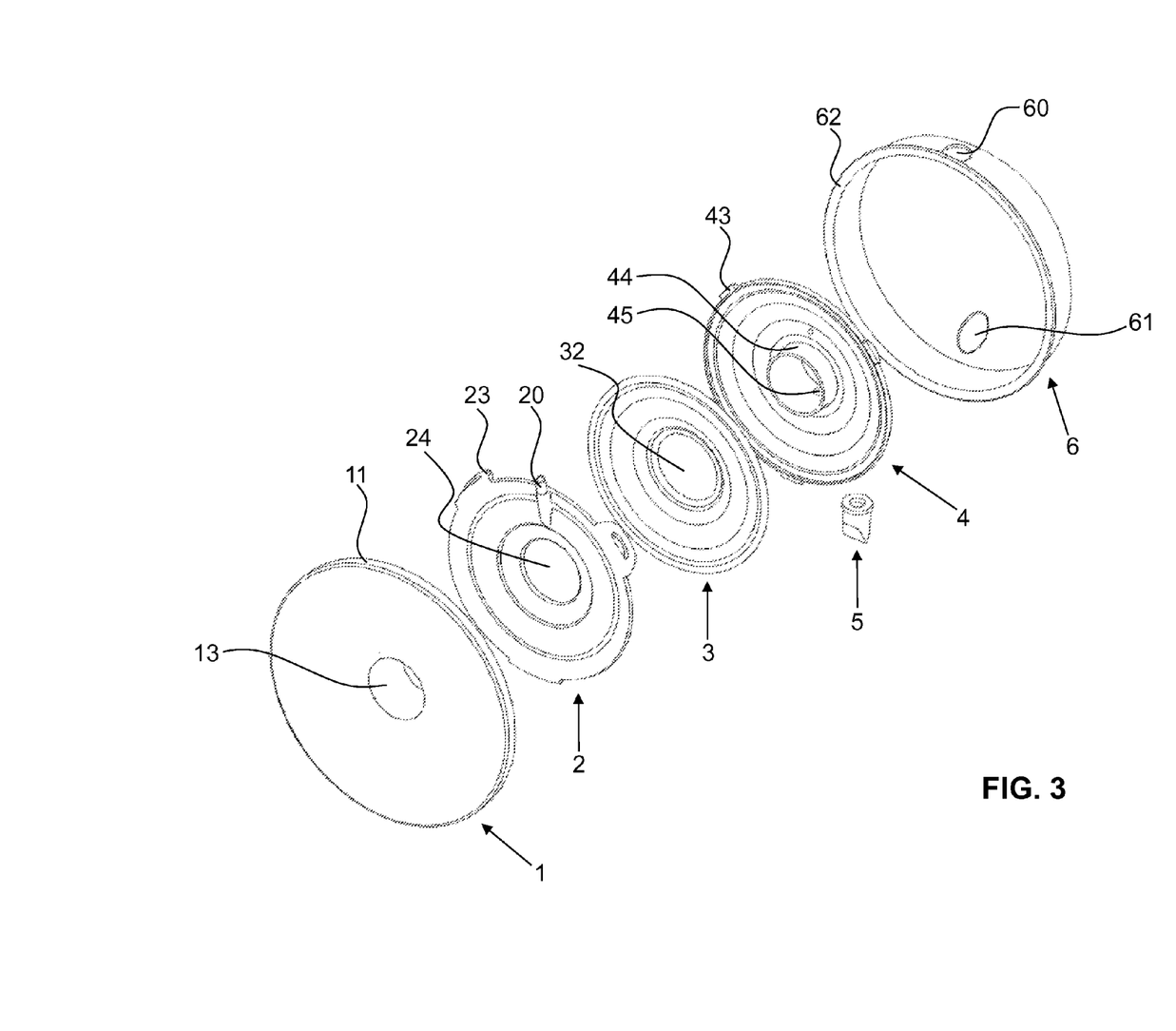
FIG. 3 shows an exploded view of the breastshield unit according to FIG. 1.

The individual parts of the breastshield unit 9 according to the invention can be seen clearly in FIG. 3. The breast interface 1 already described forms a first outer wall, and the shell 6 forms an opposite, second outer wall of the unit 9. Arranged between them are a breast-side membrane housing part 2, a membrane 3, a membrane housing part 4 facing away from the breast, and a non-return valve 5, here a duckbill valve.

The two membrane housing parts 2, 4 are preferably made of a stiff material, in particular of plastic. They are preferably in each case formed in one piece. The membrane 3 is preferably made of a flexible material, in particular of silicone. A preferred hardness is 60 Shore A.

The individual parts, with the exception of the non-return valve 5, preferably have a round shape. The breast interface 1, the breast-side membrane housing part 2, and the membrane 3 preferably have openings 13, 24, 32 arranged flush with one another, in this case centrally. The membrane housing part 4 facing away from the breast has a stub 44, which is flush with these openings 13, 24, 32.

The membrane housing part 2 near the breast has several, in this case three, angled securing eyelets 23 on its outer circumference. These securing eyelets 23 can be pushed over corresponding securing lugs 43 of the membrane housing part 4 facing away from the breast. In this way, in combination with the inserted membrane 3, a closed membrane housing 2, 4 with a sealed annular pump chamber 46 is formed. The membrane 3 is held movably in this pump chamber 46.

Figure 4:
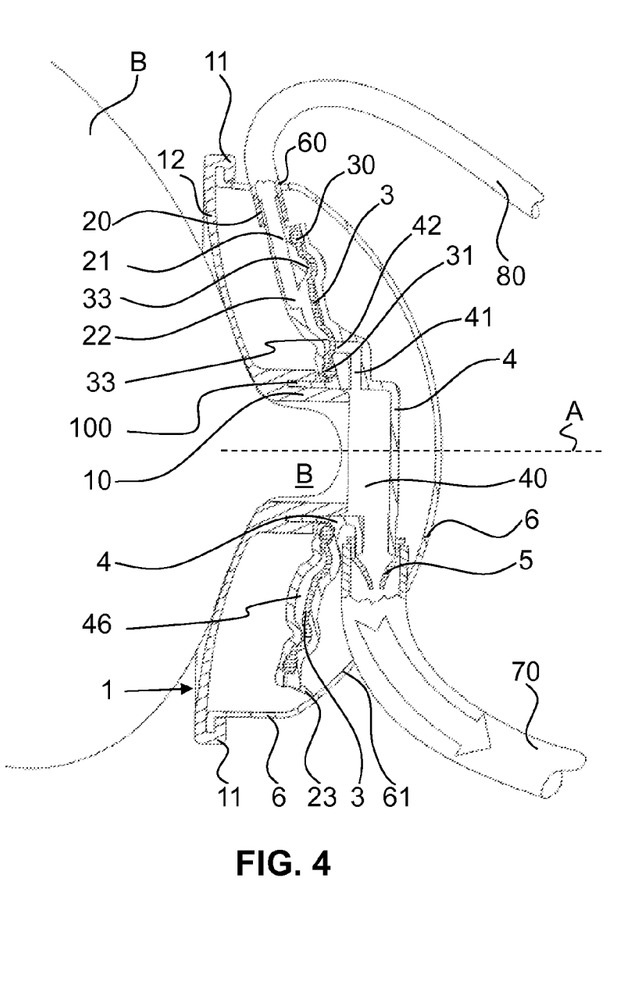
FIG. 4 shows a longitudinal section through the breastshield unit according to FIG. 1 when placed on a mother's breast and with the milk port open.
Figure 5:
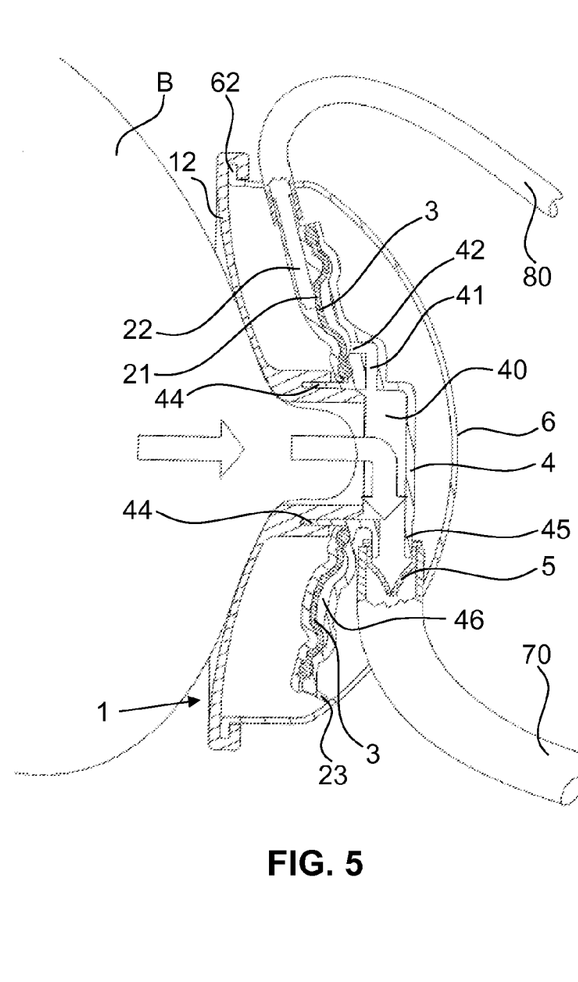
FIG. 5 shows the breastshield unit according to FIG. 4 with the milk port closed.

This assembled state can be seen clearly in FIGS. 4 and 5. The one-piece, annular membrane 3, preferably provided with bulges 33, has an outer and an inner securing bead 30, 31, which are held in corresponding seats, are fixed in position and have a sealing action. These seats are formed by the two housing parts 2, 4 joined together. In the area of the membrane 3, the two housing parts 2, 4 form the annular pump chamber 46 with a pump-side opening 22 and a breast-side opening 42.

The pump-side opening 22 leads to the vacuum line 80 via a vacuum channel 21, which ends in a port 20. The breast-side opening 42 leads to an underpressure chamber 40 via a connecting channel 41. This underpressure chamber 40 is limited by the membrane housing part 4 facing away from the breast and is open in the direction of the breast interface 1. The underpressure chamber 40 has a milk port 45, which is preferably arranged at that end of the underpressure chamber 40 remote from the connecting channel 41. The non-return valve 5 is arranged in this milk port 45. When there is an overpressure in the vacuum chamber 40 relative to the atmospheric pressure, the non-return valve 5 opens and establishes a connection to the milk line 70. When there is an underpressure in the vacuum chamber 40, the non-return valve 5 closes and thus interrupts the connection to the milk line 70. The non-return valve 5 can be fixedly connected to the milk port 45 or to the milk line 70.

In its upper area, the vacuum chamber 40 merges into the stub 44. The stub 10 of the breast interface 1 is pushed over this stub 44. This stub 10 has an annular receiving groove 100 for this purpose.

As can be seen here, the breast interface 1 preferably has a base part 12 with a slightly funnel-shaped configuration and the stub 10 formed integrally thereon. This stub defines a centre axis A. In FIGS. 4 and 5, the breast interface 1 is placed on a human mother's breast, such that the nipple B protrudes into the receiving part, which is formed by stub 10 and stub 44. In this way, this opening of the underpressure chamber 40 is closed sealingly.

If a pulsing vacuum or a vacuum with changing frequency and intensity is now generated by the suction pump unit 8 and conveyed through the vacuum line 80 to the pump chamber 46, the membrane 3 is drawn towards the pump-side opening 22 and closes the latter. This situation is shown in FIG. 5. By the movement of the membrane 3, an underpressure is generated in the pump chamber 46 and therefore in the underpressure chamber 40. Milk is expressed from the mother's breast, as is symbolized by the arrows in FIG. 5. The underpressure chamber 40 fills at least partially with breastmilk.

If the underpressure applied in the vacuum channel 21 is now reduced according to the suction cycle generated by the breastpump or is even lowered to atmospheric pressure, the membrane 3 is drawn towards the breast-side opening 42, closes the latter and thus frees the pump-side opening 22. In this way, the pressure in the underpressure chamber 40 increases and the non-return valve 5 opens. The expressed milk can flow off through the milk line 70. This situation is shown in FIG. 4.

The membrane 3 also moves in the rhythm of the underpressure generated by the suction pump unit 8 and thus transfers the rhythm and the vacuum level onwards to the underpressure chamber 40. By virtue of the relatively large surface of the membrane 3 and the small volume of the underpressure chamber 40, a relatively small stroke is sufficient to ensure that an underpressure necessary for expressing milk is generated in the area of the nipple B.

Figure 6:
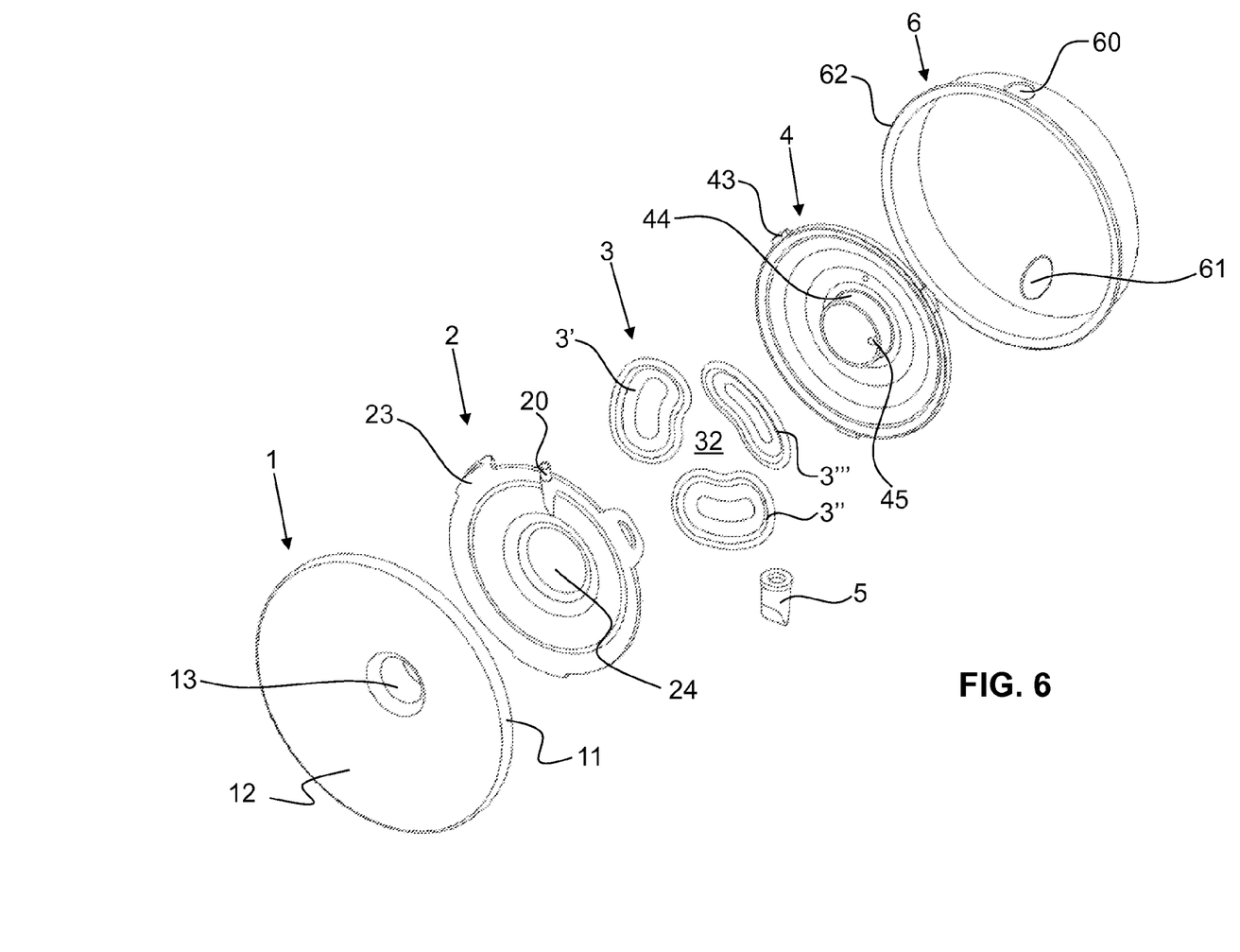
FIG. 6 shows an exploded view of a second embodiment of the breastshield unit according to the invention.

FIG. 6 shows a second illustrative embodiment. It has basically the same parts as the first illustrative embodiment. However, the membrane 3 is in several pieces. Here, three membrane parts 3', 3", 3'" are present, which are held in corresponding seats of the membrane housing 2, 4 and can again move to and fro in a pump chamber between pump-side openings and breast-side openings. The membrane parts 3', 3", 3'" enclose a circular opening, through which the stub 10 of the breast interface 1 and the stub 44 of the membrane housing part 4 facing away from the breast once again pass.

Figure 7:
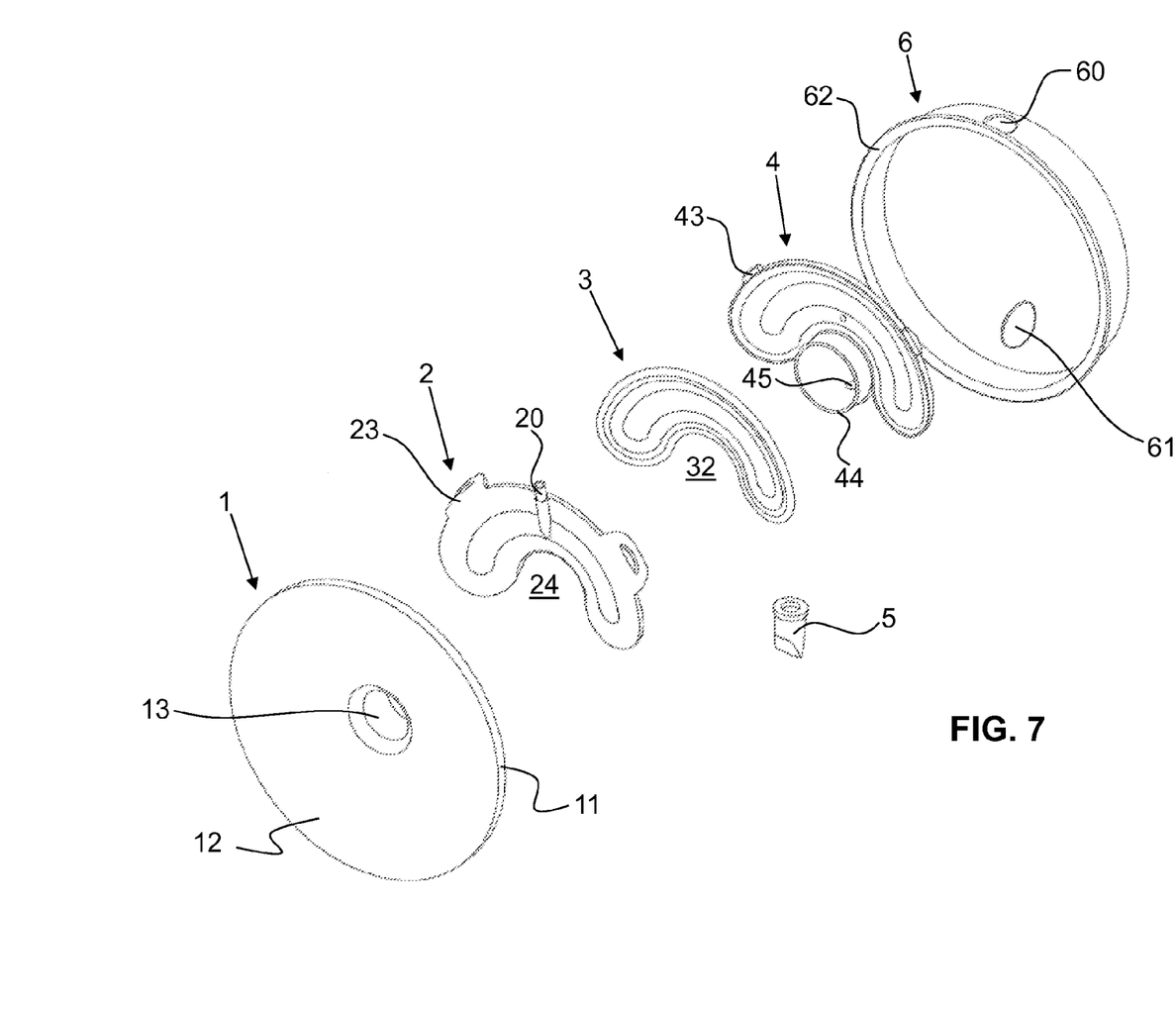
FIG. 7 shows an exploded view of a third embodiment of the breastshield unit according to the invention.
Figure 8:
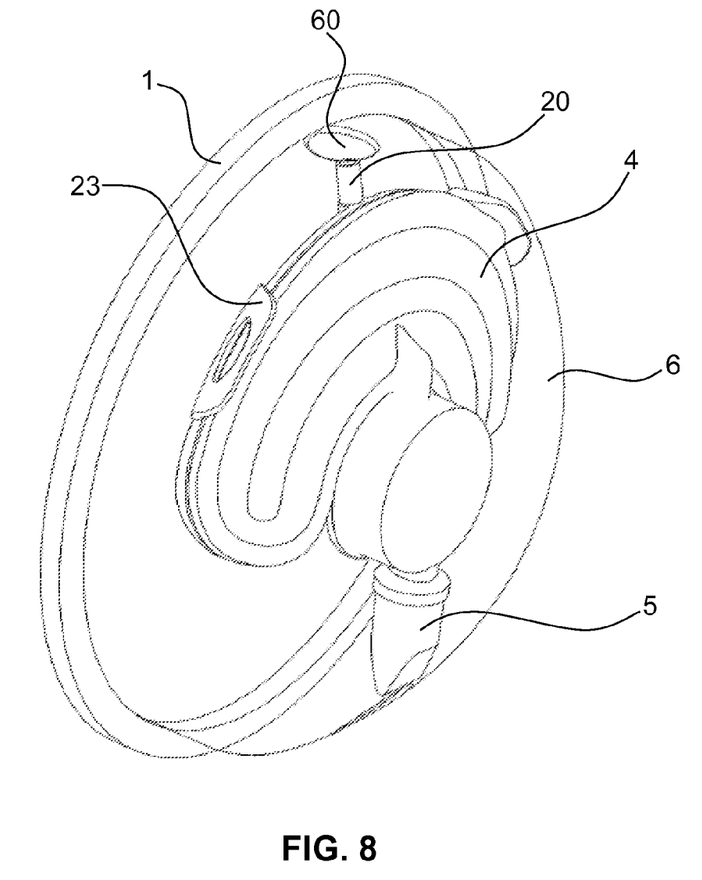
FIG. 8 shows the breastshield unit according to FIG. 7 in the assembled state.

FIGS. 7 and 8 show a third illustrative embodiment. Here, the membrane 3 is once again designed in one piece but forms only a partial area of a ring. The membrane 3 can also be kidney-shaped. The membrane 3 only partially encloses the two aforementioned stubs 10, 44. Accordingly, the membrane housing parts 2, 4 likewise only have a cross section in the shape of a partial circle. In the membrane housing part 4 facing away from the breast, the stub 44, naturally with a round cross section and with an entirely closed jacket, is formed integrally on the partial circle. The shell 6 is shown in transparent form in FIG. 8 such that the membrane housing part 4 facing away from the breast can be clearly seen.

Figure 9:
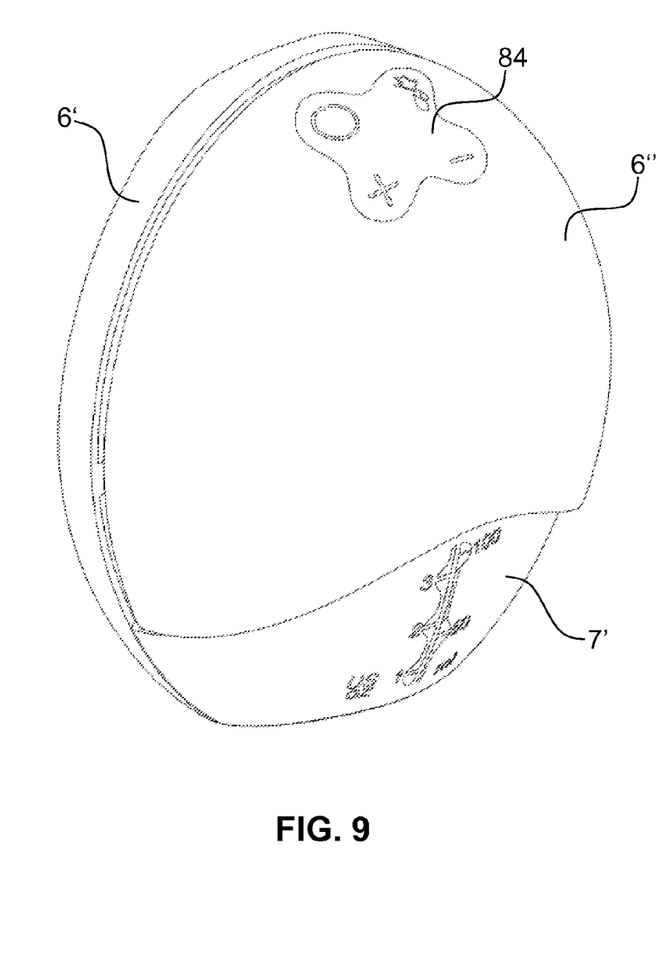
FIG. 9 shows a perspective view of a breastpump according to the invention with breastshield unit, integrated milk collection container and integrated vacuum pump.
Figure 10:
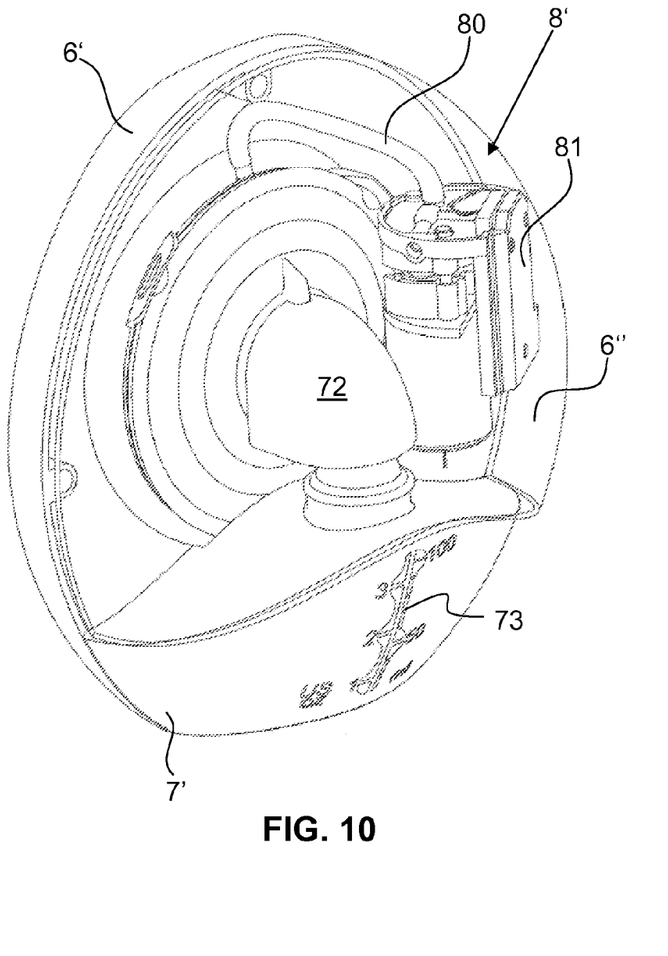
FIG. 10 shows the breastpump according to FIG. 9 without cover.
Figure 11:
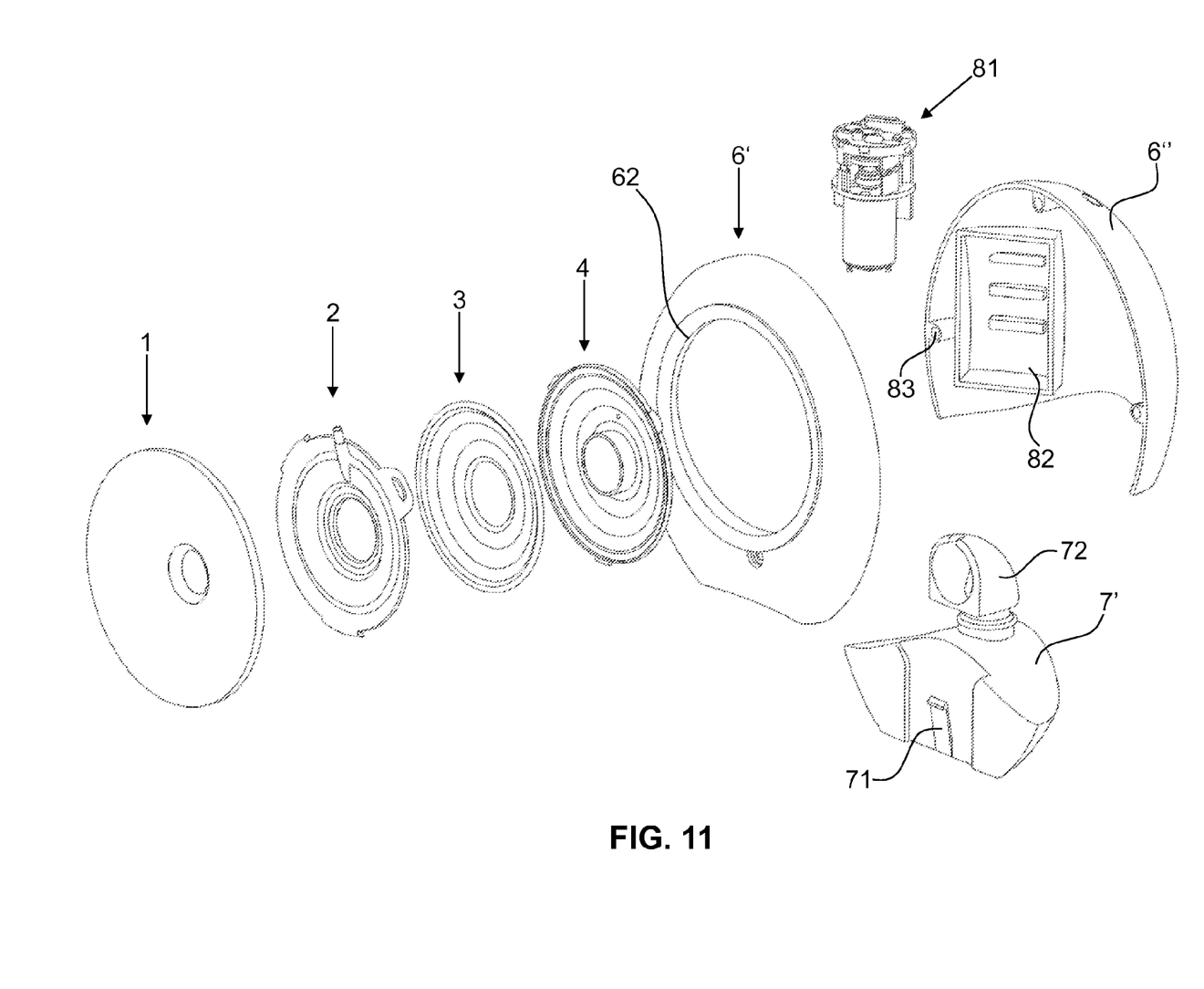
FIG. 11 shows an exploded view of the breastpump according to FIG. 9.

FIGS. 9 to 11 show another illustrative embodiment in which the breastshield unit is designed as a complete breastpump with an integrated suction pump unit 8'. The breast interface 1, the membrane housing parts 2, 4 and the membrane 3 correspond to the embodiment according to FIGS. 1 to 5. It is also possible, however, for the embodiments according to FIGS. 6 to 8 to be used in such a pump.

Instead of the dome-shaped shell 6, however, a shell ring 6' is now present. The shell ring 6' is preferably once again rigid and in particular made of plastic. The shell ring 6' has an opening with a circumferential securing flange 62 for securing the breast interface 1. A rear face, i.e. the face directed away from the breast, is partially closed by a cover 6". A pump seat 82, in which a vacuum pump 81 is held, is formed integrally in this cover 6". A power source is preferably integrated in this vacuum pump 81. The vacuum pump 81 is preferably a diaphragm vacuum pump of a known type, which is operated by means of an electric motor.

Control elements 84 for activating the vacuum pump 81 are present on the outside of the cover 6". The breastpump unit further comprises a corresponding control system by which the commands entered by the user via the control elements 84 are transferred to the vacuum pump. This control system can be arranged separately in the housing or can be integrated in the vacuum pump 81.

A milk collection container 7' is arranged in the lower area adjoining the cover 6". It is preferably made of plastic like the cover 6". A locking lug 71 is integrally formed on this milk collection container 7' and can engage in a corresponding recess (not shown in the Figures) of the shell ring 6'. In this way, the milk collection container 7' is connected releasably to the shell ring 6'. The milk collection container 7' additionally has a coupling part 72 with an integrated valve (not shown here) which can be plugged onto the milk port 45 of the membrane housing part 4 facing away from the breast, such that the expressed milk can flow from the underpressure chamber 40 into the interior of the milk collection container 7'. The valve corresponds to the non-return valve 5 in the embodiments described above. A filling level indicator 73 in the form of a scale is preferably present on the milk collection container 7'. The milk collection container 7' is either transparent or partially transparent in its entirety or it has a transparent or partially transparent window in the area of the scale 73.

The breastshield unit according to the invention permits a separation of media in the area near the breast. The breastshield unit is small and easy to clean and is particularly suitable for use as a hands-free breastpump unit that can be worn in the bra.

The invention claimed is:

1. A breastshield unit for expressing human breastmilk, wherein the breastshield unit has:
   a receiving part for receiving a human nipple;
   an underpressure chamber for applying an underpressure to the nipple, wherein the receiving part opens into the underpressure chamber,
   a membrane for generating an underpressure in the underpressure chamber,
   a vacuum port that can be connected to a vacuum pump, and
   a pump chamber having a first outlet, which leads to the vacuum port, and a second outlet, which leads to the underpressure chamber,
   wherein the membrane is arranged in the pump chamber and separates the vacuum port from the underpressure chamber, and wherein the membrane is designed in one or more pieces and at least partially surrounds the receiving part.

2. The breastshield unit according to claim 1, wherein the membrane surrounds an opening in the shape of a circle or partial circle.

3. The breastshield unit according to claim 2, wherein the membrane is formed in one piece and has an annular shape.

4. The breastshield unit according to claim 2, wherein the membrane has at least two individual parts, wherein the individual parts in the assembled state enclose a circle or a partial circle.

5. The breastshield unit according to claim 1, further comprising a breast-side membrane housing part and a membrane housing part facing away from the breast, wherein the membrane housing parts form a common membrane housing, and wherein the membrane is held movably between the two membrane housing parts.

6. The breastshield unit according to claim 1, wherein the membrane has a frustoconical shape in a rest position.

7. The breastshield unit according to claim 1, further comprising a breast interface for placing on a mother's breast, wherein the breast interface can be secured on a housing shell enclosing the membrane.

8. The breastshield unit according to claim 7, wherein the breast interface has a frustoconical or cylindrical first stub for receiving the nipple, wherein the first stub can be connected to a second stub of the underpressure chamber, and wherein the first stub and the second stub form the receiving part.

9. The breastshield unit according to claim 1, further comprising a milk collection container integrated in the breastshield unit, wherein the milk collection container is arranged releasably on the rest of the breastshield unit.

10. A breastpump with a breastshield unit according to claim 1, further comprising a vacuum line and a vacuum pump, wherein the vacuum line connects the vacuum port to the vacuum pump.

11. The breastpump according to claim 10, wherein the breastpump unit has a housing shell, which encloses the membrane and in which the vacuum pump is arranged.

12. A breastshield unit for expressing human breastmilk, wherein the breastshield unit has:
   a receiving part for receiving a nipple, wherein the receiving part defines a centre axis;
   an underpressure chamber for applying an underpressure to the nipple, wherein the receiving part opens into the underpressure chamber,
   a membrane for generating an underpressure in the underpressure chamber,
   a vacuum port that can be connected to a vacuum pump, and
   a pump chamber having a first outlet, which leads to the vacuum port, and a second outlet, which leads to the underpressure chamber,
   wherein the membrane is arranged in the pump chamber and separates the vacuum port from the underpressure chamber, and wherein viewed in the direction of extension of the centre axis, the membrane is arranged on a side of the underpressure chamber facing towards the nipple.

13. The breastshield unit according to claim 12, wherein the membrane surrounds an opening in the shape of a circle or partial circle.

14. The breastshield unit according to claim 13, wherein the membrane is formed in one piece and has an annular shape.

15. The breastshield unit according to claim 13, wherein the membrane has at least two individual parts, wherein the individual parts in the assembled state enclose a circle or a partial circle.

16. The breastshield unit according to claim 12, further comprising a breast-side membrane housing part and a membrane housing part facing away from the breast, wherein the membrane housing parts form a common membrane housing, and wherein the membrane is held movably between the two membrane housing parts.

17. The breastshield unit according to claim 12, wherein the membrane has a frustoconical shape in a rest position.

18. The breastshield unit according to claim 12, further comprising a breast interface for placing on a mother's breast, wherein the breast interface can be secured on a housing shell enclosing the membrane.

19. The breastshield unit according to claim 18, wherein the breast interface has a frustoconical or cylindrical first stub for receiving the nipple, wherein the first stub can be connected to a second stub of the underpressure chamber, and wherein the first stub and the second stub form the receiving part.

20. The breastshield unit according to claim 12, further comprising a milk collection container integrated in the breastshield unit, wherein the milk collection container is arranged releasably on the rest of the breastshield unit.

21. A breastpump with a breastshield unit according to claim 12, further comprising a vacuum line and a vacuum pump, wherein the vacuum line connects the vacuum port to the vacuum pump.

22. The breastpump according to claim 21, wherein the breastpump unit has a housing shell, which encloses the membrane and in which the vacuum pump is arranged.

23. A breastshield unit for expressing human breastmilk, wherein the breastshield unit has:
- a receiving part for receiving a nipple of a mother's breast, wherein the receiving part defines a centre axis;
- an underpressure chamber for applying an underpressure to the nipple, wherein the receiving part opens into the underpressure chamber;
- a milk port for connecting the underpressure chamber to a milk collection container,
- a membrane for generating an underpressure in the underpressure chamber,
- a vacuum port that can be connected to a vacuum pump, and
- a pump chamber having a first outlet, which leads to the vacuum port, and a second outlet, which leads to the underpressure chamber,
- wherein the membrane is arranged in the pump chamber and separates the vacuum port from the underpressure chamber, and wherein viewed in the direction of extension of the centre axis, the membrane is arranged on a side of the milk port facing towards the mother's breast.

24. The breastshield unit according to claim 23, wherein the membrane surrounds an opening in the shape of a circle or partial circle.

25. The breastshield unit according to claim 24, wherein the membrane is formed in one piece and has an annular shape.

26. The breastshield unit according to claim 24, wherein the membrane has at least two individual parts, wherein the individual parts in the assembled state enclose a circle or a partial circle.

27. The breastshield unit according to claim 23, further comprising a breast-side membrane housing part and a membrane housing part facing away from the breast, wherein the membrane housing parts form a common membrane housing, and wherein the membrane is held movably between the two membrane housing parts.

28. The breastshield unit according to claim 23, wherein the membrane has a frustoconical shape in the rest position.

29. The breastshield unit according to claim 23, further comprising a breast interface for placing on a mother's breast, wherein the breast interface can be secured on a housing shell enclosing the membrane.

30. The breastshield unit according to claim 29, wherein the breast interface has a frustoconical or cylindrical first stub for receiving the nipple, wherein the first stub can be connected to a second stub of the underpressure chamber, and wherein the first stub and the second stub form the receiving part.

31. The breastshield unit according to claim 23, further comprising a milk collection container integrated in the breastshield unit, wherein the milk collection container is arranged releasably on the rest of the breastshield unit.

32. A breastpump with a breastshield unit according to claim 23, further comprising a vacuum line and a vacuum pump, wherein the vacuum line connects the vacuum port to the vacuum pump.

33. The breastpump according to claim 32, wherein the breastpump unit has a housing shell, which encloses the membrane and in which the vacuum pump is arranged.

\* \* \* \* \*